US009424394B2

(12) United States Patent
Simon

(10) Patent No.: US 9,424,394 B2
(45) Date of Patent: Aug. 23, 2016

(54) METHOD AND SYSTEM FOR GENERATING PERSONALIZED HEALTH INFORMATION DISPLAY

(71) Applicant: Verizon Patent and Licensing Inc., Basking Ridge, NJ (US)

(72) Inventor: Adam J. Simon, Keller, TX (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 236 days.

(21) Appl. No.: 14/105,352

(22) Filed: Dec. 13, 2013

(65) Prior Publication Data

US 2015/0169838 A1     Jun. 18, 2015

(51) Int. Cl.
*G06F 19/00*     (2011.01)

(52) U.S. Cl.
CPC ........ *G06F 19/3431* (2013.01); *G06F 19/3406* (2013.01); *G06F 19/3418* (2013.01)

(58) Field of Classification Search
None
See application file for complete search history.

(56) References Cited

U.S. PATENT DOCUMENTS

| | | | | |
|---|---|---|---|---|
| 2,112,516 A * | 3/1938 | Browne | ................. | G01R 15/09 116/300 |
| 2011/0077968 A1* | 3/2011 | Kelly | .................... | G06F 19/345 705/3 |
| 2012/0235821 A1* | 9/2012 | DiBenedetto | ...... | A63B 24/0062 340/573.1 |
| 2013/0138230 A1* | 5/2013 | Landers | .................. | G06F 17/40 700/91 |
| 2013/0211214 A1* | 8/2013 | Olsen | ..................... | A61B 5/742 600/316 |
| 2014/0089836 A1* | 3/2014 | Damani | .............. | G06F 19/3418 715/771 |
| 2014/0214454 A1* | 7/2014 | Kahn | ..................... | G06Q 50/22 705/3 |
| 2014/0267299 A1* | 9/2014 | Couse | .................. | G06T 11/206 345/440.2 |

OTHER PUBLICATIONS

Oracle Help Center, Using Gauge Components, Jun. 2013, Oracle, https://web.archive.org/web/20130929191007/http:/docs.oracle.com/middleware/1212/adf/ADFUI/dv_gauge.htm, pp. 1 and 27.*

* cited by examiner

*Primary Examiner* — William Bashore
*Assistant Examiner* — Daniel Parcher

(57) ABSTRACT

An approach for providing personalized information regarding one or more physiological conditions associated with a user is described. A personal health platform calculates a minimum value, a maximum value, or a combination thereof for a physiological condition of a user. The personal health platform senses a measured value for the physiological condition from the user. The personal health platform further presents a user interface depicting the measured value relative to the minimum value, the maximum value, a historical measured value for the user, or a combination thereof, wherein the user interface depicts the measured value, the minimum value, the maximum value, or a combination thereof on one or more ring-based graphical elements, and wherein the one or more ring-based graphical elements correspond to a measurement range for the physiological condition.

13 Claims, 11 Drawing Sheets

METHOD AND SYSTEM FOR GENERATING PERSONALIZED HEALTH INFORMATION DISPLAY

BACKGROUND INFORMATION

Application developers and service providers are continually challenged to deliver value and convenience to consumers by providing compelling applications and delivery platforms. One area of interest has been providing applications and/or services that enable clinicians to help patients understand and become better aware about their physiological conditions (e.g., cholesterol, blood sugar, weight loss or gain, blood pressure, etc.). In particular, there is an interest to bring and effectively display this information on mobile devices (e.g., mobile phones, phablets, tablets, etc.). However, many of today's applications and/or services are based on general population metrics (e.g., average height, weight, and/or age ranges) to the detriment of users suffering from a chronic disease such as heart failure or diabetes and therefore do not fall within the general population metrics.

Based on the foregoing, there is a need for providing personalized information regarding one or more physiological conditions associated with a user.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENT

An apparatus, method and software for providing personalized information regarding one or more physiological conditions associated with a user is described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention.

Figure 1:
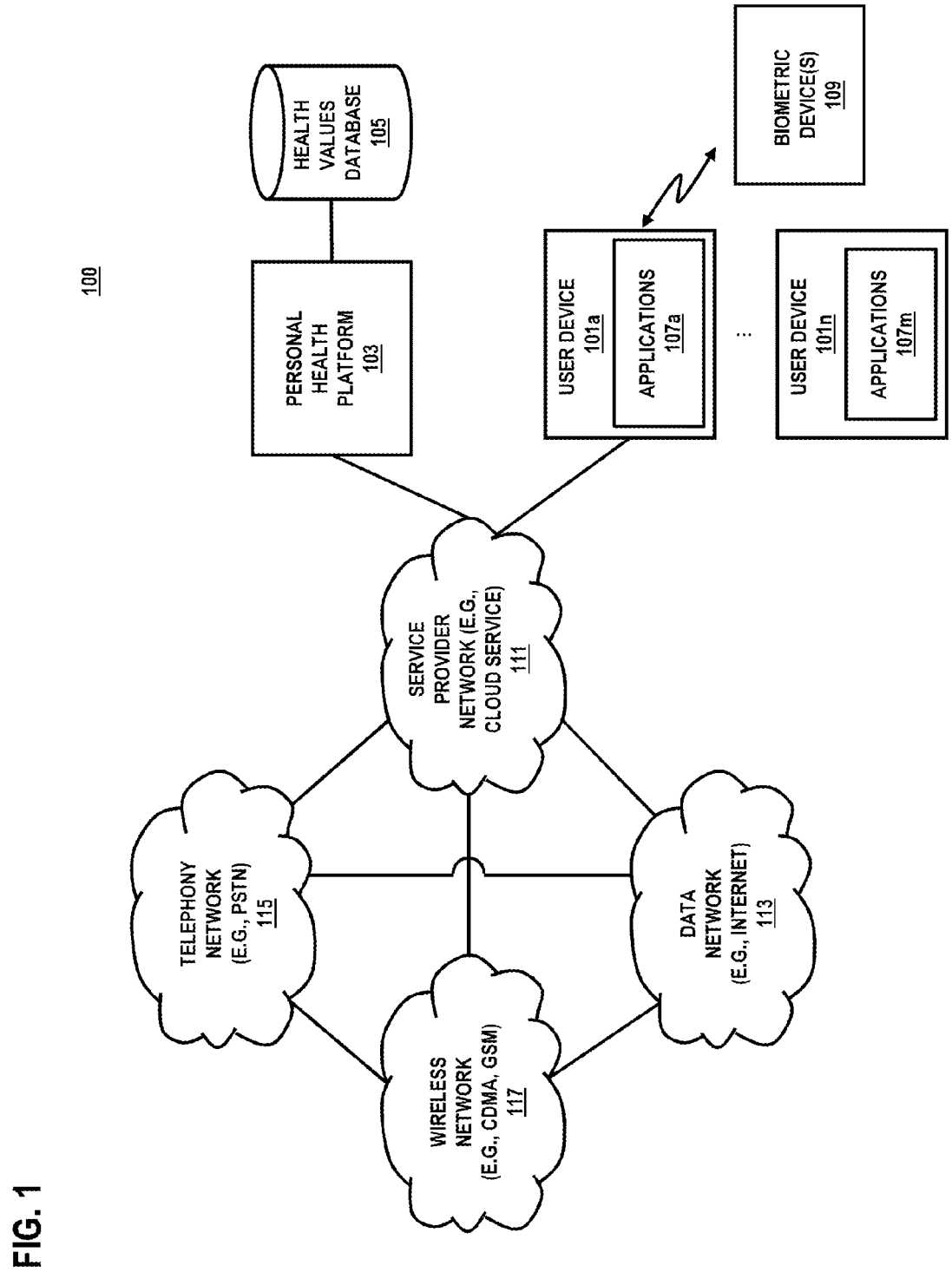
FIG. 1 is a diagram of a system for providing personalized information regarding one or more physiological conditions associated with a user, according to one embodiment.

FIG. 1 is a diagram of a system for providing personalized information regarding one or more physiological conditions associated with a user, according to one embodiment. As previously discussed, there is increasing interest among application developers and services providers to provide applications and/or services that enable clinicians and users alike to understand and learn about one or more physiological conditions associated with a user. One way to achieve this is to display information derived from a biometric device (e.g., a blood pressure cuff) on a mobile device (e.g., a mobile phone, a phablet, or a tablet). However, many of today's applications and/or services are based on general population metrics (e.g., average height, weight, again, etc.) to the detriment of users that do not fall into such generalized categories such as those suffering from chronic diseases (e.g., heart failure or diabetes).

To address this problem, a system 100 introduces the capability to provide personalized information regarding one or more physiological conditions associated with a user, according to one embodiment. For the purpose of illustration, the system 100 that enables a user and/or a medical professional (e.g., a clinician) to view and understand one or more physiological conditions (e.g., cholesterol, glucose, bodyweight, blood pressure, etc.) associated with a user via one or more user devices 101a-101n (e.g., a mobile phone, a phablet, and/or a tablet)(also referred to collectively as user devices 101) is described with respect to a personal health platform 103. In one embodiment, the personal health platform 103 may include or be associated with a health values database 105. In one example embodiment, the personal health platform 103 may exist in whole or in part within a user device 101, or independently and the health values database 105 may exist in whole or in part within the personal health platform 103. By way of example, the health values database 105 may include a minimum value, a maximum value, one or more historical measured values, or a combination thereof for one or more physiological conditions of a user.

In one embodiment, the user devices 101 also include or have access to one or more applications 107a-107m (also collectively referred to as applications 107). By way of example, the applications 107 may include one or more health-based applications (e.g., heart monitoring applications, exercised-based applications, dietary applications, etc.). In addition, the user devices 101 are associated with one or more biometric devices 109 (e.g., a blood pressure cuff, a glucose monitor, a pulse oximeter, a weight scale, etc.) via one or more short range wireless communications including Bluetooth®, near field communications (NFC), or a combination thereof.

As seen in FIG. 1, the user devices 101, the personal health platform 103, the health values database 105, the applications 107 and other elements of system 100 may be configured to communicate via a service provider network 111 (e.g., a cloud service). According to certain embodiments, one or more networks, such as data network 113, telephony network 115, and/or wireless network 117, can interact with the service provider network 111. Networks 111-117 may be any suitable wireline and/or wireless network, and be managed by one or more service providers. For example, telephony network 115 may include a circuit-switched network, such as the public switched telephone network (PSTN), an integrated services digital network (ISDN), a private branch exchange (PBX), or other like network.

Networks 111-117 may employ various technologies for enabling wireless communication including, for example, code division multiple access (CDMA), long term evolution (LTE), enhanced data rates for global evolution (EDGE), general packet radio service (GPRS), mobile ad hoc network (MANET), global system for mobile communications (GSM), Internet protocol multimedia subsystem (IMS), universal mobile telecommunications system (UMTS), etc., as well as any other suitable wireless medium, e.g., microwave access (WiMAX), wireless fidelity (Wi-Fi), satellite, and the like. Meanwhile, data network 113 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Still further, the communication provider network may embody circuit-switched and/or packet-switched networks that include facilities to provide for transport of circuit-switched and/or packet-based communications. It is further contemplated that networks 111-117 may include components and facilities to provide for signaling and/or bearer communications between the various components or facilities of system 100. In this manner, the communication networks 111-117 may embody or include portions of a signaling system 7 (SS7) network, Internet protocol multimedia subsystem (IMS), or other suitable infrastructure to support control and signaling functions.

It is noted that the user devices 101 may be any type of mobile terminal, fixed terminal, or portable terminal including a mobile handset, station, unit, device, multimedia computer, multimedia tablet, Internet node, communicator, desktop computer, laptop computer, Personal Digital Assistants (PDAs), smartphone or any combination thereof. It is also contemplated that the user devices 101 can support any type of interface for supporting the presentment or exchanging of data. In addition, the user devices 101 may facilitate various input means for receiving and generating information, including touch screen capability, keyboard and keypad data entry, voice-based input mechanisms and the like. Any known and future implementations of user devices 101 are applicable.

In one embodiment, the system 100 calculates a minimum value, a maximum value, or a combination thereof for a physiological condition of a user. For example, the minimum and maximum values may correspond to good, average, and bad levels of the one or more physiological conditions associated with the user (e.g., his or her cholesterol level, glucose level, bodyweight, blood pressure, etc.). As a result, it is contemplated that users can be more actively involved in their own health management, which can encourage users to better follow physician-directed care plans and can also help users to manage chronic illnesses more effectively.

In one embodiment, the system 100 generates the minimum value, the maximum value, or a combination thereof based on manual input. More specifically, the input may be provided by a user (e.g., setting weekly goals or achievable goals between check-ups), a medical professional (e.g., a clinician setting up a directed care plan), an authorized third-party (e.g., a user's insurance company), or a combination thereof. In one example use case, a clinician may manually input the minimum and maximum values for systolic and diastolic pressures associated with a user. For example, systolic and diastolic levels for an average adult age 20 or over are generally less than 120 and 80 millimeter of mercury (mm/Hg), respectively, however, these maximum levels may not apply to a user with a chronic illness and therefore must be personalized by a medical professional, for example, to be useful.

In one embodiment, the system 100 senses a measured value for the physiological condition from the user. In particular, the system 100 is connected to one or more biometric devices such as a blood pressure cuff, a glucose monitor, a pulse oximeter, a weight scale, etc. In an exemplary embodiment it is contemplated that the system 100 can sense the measured value from the one or more biometric devices via one or more short range wireless communications including Bluetooth®, NFC, or a combination thereof.

In one embodiment, the system 100 monitors the physiological condition of the user over a period of time to generate a plurality of historical measured values for the user. For example, the measured values may cover the entire period of treatment for a user or the measured values may correspond to a period of time between visits. In addition, a user can input a customized period of time (e.g., a week or weekend). In one embodiment, the system 100 calculates the minimum value, the maximum value, or a combination thereof based on the plurality of historical measured values. For example, the system 100 may determine that over a period of time (e.g., a year) that the minimum weight value for a user was 210 pounds (lbs.) and that the maximum weight value for the user was 230 lbs. As a result, the system 100 can calculate the minimum value as 210 lbs. and the maximum value as 230 lbs. for the physiological condition of bodyweight based on the plurality of historical measured values.

In one embodiment, the system 100 presents a user interface depicting the measured value relative to the minimum value, the maximum value, a historical measured value, or a combination thereof. More specifically, the system 100 presents the user interface depicting the measured value, the minimum value, the maximum value, or a combination thereof on one or more ring-based graphical elements, wherein the one or more ring-based graphical elements correspond to a measurement range for the physiological condition (e.g., blood sugar). Further, in one embodiment, the user interface depicts the measured value relative to the minimum value, the maximum value, the historical measured value, or a combination thereof based on color. For example, a good measured value relative to the user's personalized minimum and maximum values can be rendered by the system 100 as a green color, an average measured value rendered as a yellow color, and a bad measured value rendered as a red color. In one embodiment, the system 100 can present the descriptive terms "good," "average," and/or "bad" based on the measured value sensed for the physiological condition. As a result, the system 100 can present the measured value in such a way that the user is able to easily determine whether his or her measured value is good, average, or bad. Similarly, the system 100 can present the measured value in such a way that the user is able to easily determine whether his or her measured value is trending up (e.g., presented with an up arrow) or down (e.g., presented with a down arrow) relative to one or more historical measured values for that physiological condition.

In one embodiment, the system 100 renders the one or more ring-based graphical elements in a concentric arrangement. By way of example, the system 100 can render an inner concentric ring corresponding to a minimum value and a maximum value for a physiological condition (e.g., blood sugar) and an outer concentric ring corresponding to a measured value for that physiological condition. Moreover, the system 100 can render a portion of the inner concentric ring corresponding to the minimum value as a green color, for example, the portion of the inner concentric ring corresponding to the maximum value as a red color, for example, and the portion of the outer concentric ring corresponding to the measured value the color corresponding to where the measured value falls within the minimum and the maximum values.

In one embodiment, the system 100 provides a mode of interaction for operating the user interface. In particular, the mode of interaction may be based on one or more gestures with the one or more ring-based graphical elements to present a relationship between a potential measured value, the minimum value, the maximum value, or a combination thereof. By way of example, a user can use his or her finger, for example, to drag or rotate the leading edge of the measurement range on the outer concentric circle to discover one or more corresponding values within his or her personalized minimum measurement range, maximum measurement range, or a combination thereof. For example, a user may rotate the outer concentric circle to determine how many more pounds he or she must lose to fall within his or her minimum measurement range.

In one embodiment, the system 100 can present a user interface simultaneously depicting a plurality of physiological conditions associated with the user including the respective measured values relative to the respective minimum values, maximum values, historical measured values, or a combination thereof. By way of example, the system 100 can simultaneously present the one or more measured values for a user corresponding to his or her blood sugar condition (e.g., low-density lipoprotein (LDL), high-density lipoprotein (HDL), and triglycerides). An illustrative example of this user interface is depicted in FIG. 4C. In one embodiment, it is contemplated that the system 100 can present the user interface based on device capability information, resource availability information, or a combination thereof associated with a user device. For example, if the user device 101 is a mobile phone, for example, then the system 100 may only present a user interface depicting one physiological condition or the plurality of physiological conditions in the form depicted in FIG. 4C. However, if the user device 101 is a tablet, for example, having a much larger display screen and/or increased processing power, for example, then the system 100 may present a user interface depicting a plurality of physiological conditions by rendering each of the physiological conditions as one or more ring-based graphical elements in a concentric arrangement as discussed above. In one embodiment, it is contemplated that this later arrangement can be used by a clinician to demonstrate to the user the status and possible interrelationships of the user's various physiological conditions using just one device.

In one embodiment, the system 100 can present a user interface depicting one or more of the plurality of historical measured values in relation to one another. By way of example, the system 100 can present a chart depicting a user's weight loss or weight gain over a period of time (e.g., a week, a month, etc.) so that the user may observe whether his or her physiological condition is trending up or down, for example. In addition, the system 100 can also present a user interface that depicts which values fall within a minimum measurement range, a maximum measurement range, or a combination thereof associated with the user and/or or which values are good, average, or bad, all based on color. An illustrative example of this user interface is depicted in FIG. 4D.

Figure 2:
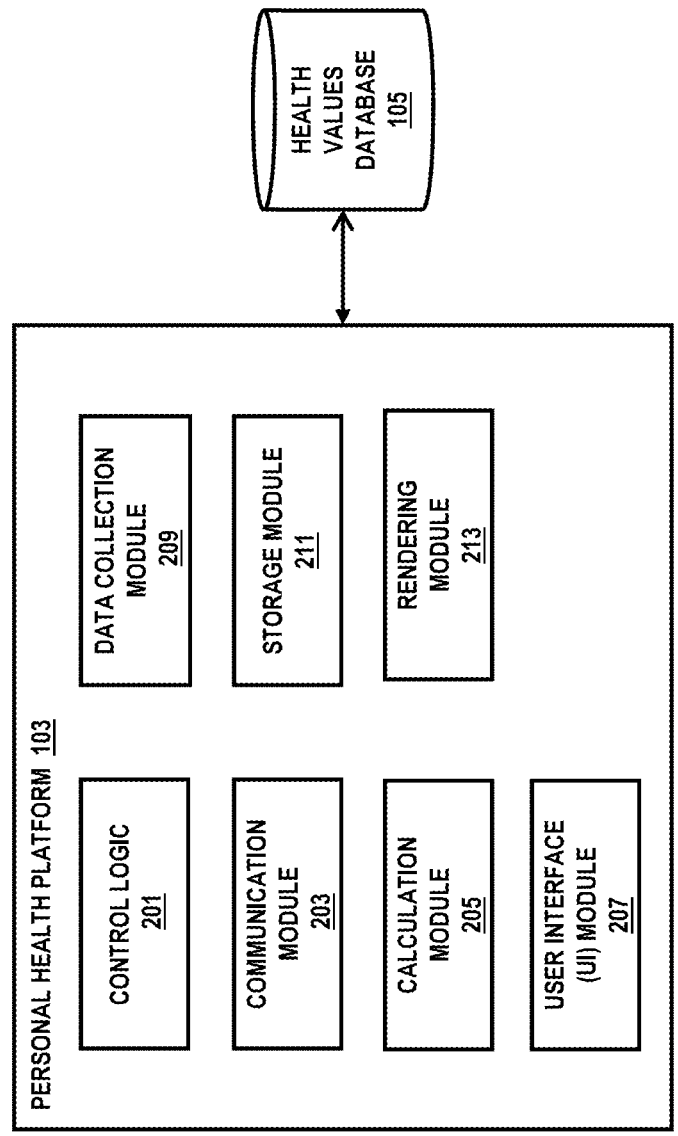
FIG. 2 is a diagram of a personal health platform, according to one embodiment.

FIG. 2 is a diagram of the components of the personal health platform 103, according to one embodiment. By way of example, the personal health platform 103 includes one or more components for providing personalized information regarding one or more physiological conditions associated with a user. It is contemplated that the functions of these components may be combined in one or more components or performed by other components of equivalent functionality. In this embodiment, the personal health platform 103 includes a control logic 201, a communication module 203, a calculation module 205, a user interface (UI) module 207, a data collection module 209, a storage module 211, and a rendering module 213.

In one embodiment, the control logic 201 oversees tasks, including tasks performed by the communication module 203, the calculation module 204, the UI module 207, the data collection module 209, the storage module 211, and the rendering module 213. For example, although the other modules may perform the actual task, the control logic 201 may determine when and how those tasks are performed or otherwise direct the other modules to perform the task. In one embodiment, the control logic 201 may be used to determine which user interface to present based on device capability information, resource availability information, or a combination thereof.

In certain embodiments, the communication module 203 is used for communication between the user devices 101, the personal health platform 103, the health values database 105, the applications 107, and the networks 111-117. In one embodiment, the communication module 203 may also be used to communicate commands, requests, data, etc. Further, in one embodiment, the communication module 203 is used to sense a measured value for a physiological condition from one or more biometric devices associated with a user. In one embodiment, it is contemplated that the communication module 203 can sense the measured value via one or more short range wireless communications including Bluetooth®, NFC, or a combination thereof.

In one embodiment, the calculation module 205 is used to calculate a minimum value, a maximum value, or a combination thereof for a physiological condition of a user. By way of example, the calculation module 205 can calculate one or more baseline values for a user based on one or more general characteristics associated with the user (e.g., age, weight, height, etc.). In one embodiment, the calculation module 205 may also be used to calculate the minimum value, the maximum value, or a combination thereof based on the plurality of historical measured values associated with the user. Consequently, the calculation module 205 can provide the personal health platform 103 with both general and personalized minimum and maximum values for a physiological condition of the user.

In one embodiment, the UI module 207, in connection with the communication module 203, is used to generate the minimum value, the maximum value, or a combination thereof based on manual input. By way of example, the UI module 207 may generate the minimum and maximum values based on one or more numeric values inputted by the user or a medical professional (e.g., a clinician) via a keypad or one or more voice recognition capabilities associated with the user device. For example, a clinician may use the UI module 207 to enter a minimum value of 60 to 110 milligrams per deciliter (mg/dl) corresponding to a user's LDL. The UI module 207 may also be used to provide a mode of interaction for operating the user interface. More specifically, the UI module 207 may be used to sense one or more gestures with the one or more ring-based graphical elements (e.g., a dragging or rotating motion of the leading edge of the measurement range on the outer concentric circle).

In one embodiment, the data collection module 209, in connection with the storage module 211, is used to monitor the physiological condition of the user over a period of time to generate a plurality of historical measured values for the user. By way of example, the data collection module 209 can make a "copy" of a measured value sensed from one or more biometric devices and the storage module 211 can store the value in the health values database 105, for example.

In one embodiment, the rendering module 213 is used to present a user interface depicting the measured value relative to the minimum value, the maximum value, a historical measured value, or a combination thereof. More specifically, the rendering module 213 can depict the measured value, the minimum value, the maximum value, or a combination thereof on one or more ring-based graphical elements corresponding to a measurement range for the physiological condition. By way of example, the rendering module 213 may depict the measured value relative to the minimum value, the maximum value, the historical measured value, or a combination thereof based on color. For example, the rendering module 213 may render a good measured value as a green color, an average measured value as a yellow color, and a bad measured value a red color. The rendering module 213 may also be used to render the one or more ring-based graphical elements in a concentric arrangement. By way of further example, the rendering module 213 may render an inner concentric ring corresponding to the minimum and maximum values of a physiological condition associated with a user and render an outer concentric ring corresponding to the measured value of the condition. As previously discussed, the rendering module 213 may also render portions of the inner and outer concentric rings in colors corresponding to the minimum and maximum values.

In one embodiment, the rendering module 213 may also be used to present a user interface simultaneously depicting a plurality of physiological conditions of the user including the respective measured values relative to the respective minimum values, maximum values, historical measured values, or a combination thereof. By way of example, the rendering module 213 can simultaneously present the one or more measured values corresponding to blood sugar (e.g., LDL, HDL, and triglycerides). As previously discussed, depending on the device capability information, the resource availability information, or a combination thereof (e.g., a mobile phone verses a tablet), the rendering module 213 also may be used to present a user interface depicting a concentric arrangement of the one or more ring-based graphical elements for each physiological condition simultaneously (e.g., presented across the length of the tablet). Further, the rendering module 213 also may be used to present a user interface depicting one or more of the plurality of historical measured values in relation to one another (e.g., as a trending report or trending graph).

Figure 3:
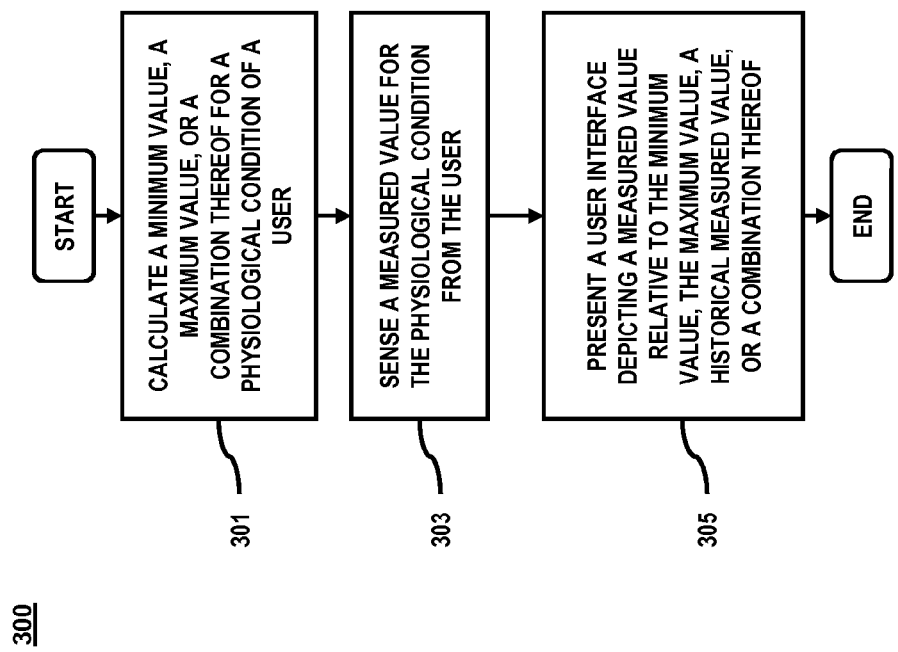
FIGS. 3-5 are flowcharts of processes for providing personalized information regarding one or more physiological conditions associated with a user, according to various embodiments.
Figure 4:
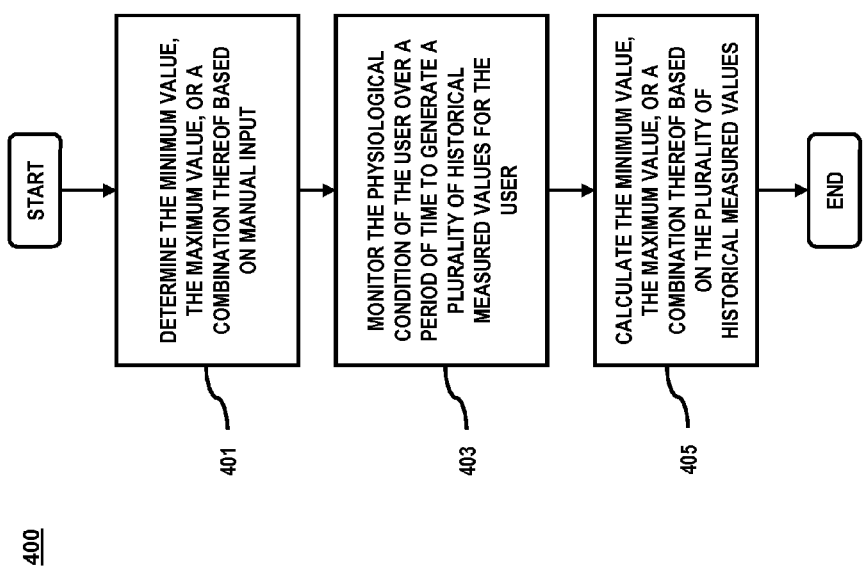
Figure 5:
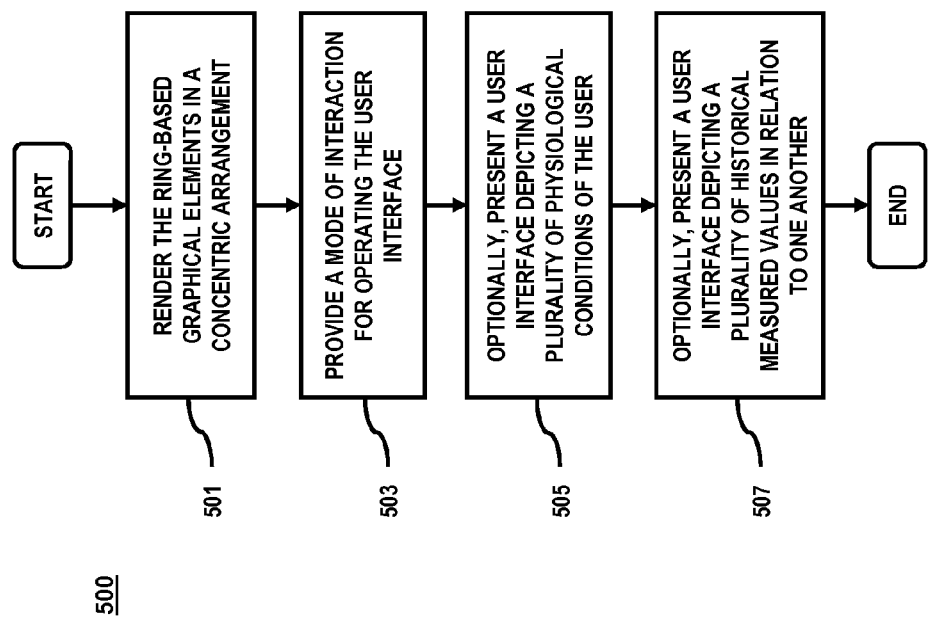
Figure 8:
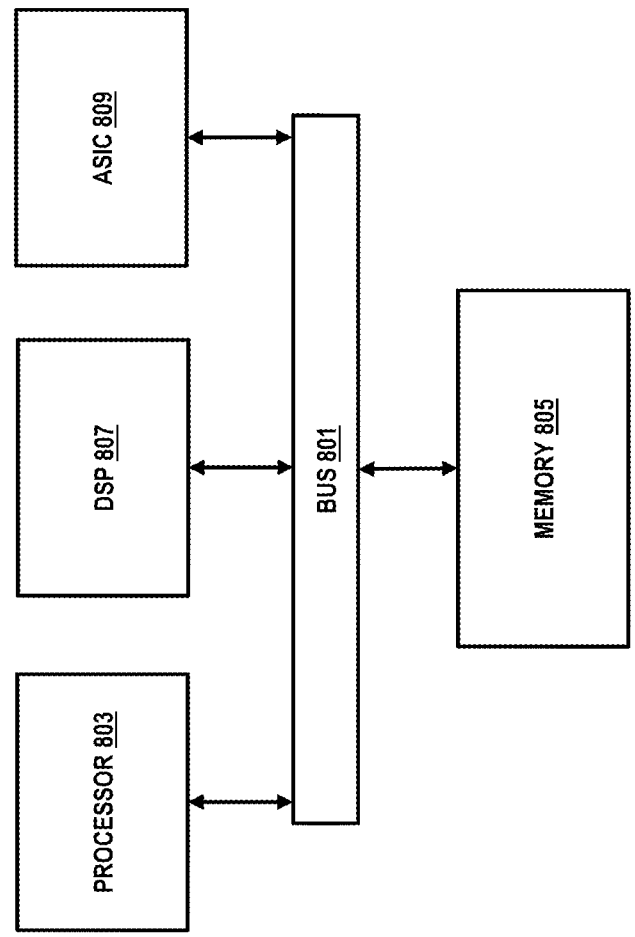
FIG. 8 is a diagram of a chip set that can be used to implement an embodiment of the invention.

FIGS. 3-5 are flowcharts of processes for providing personalized information regarding one or more physiological conditions associated with a user, according to various embodiments. In one embodiment, the personal health platform 103 performs the process 300 and is implemented in, for instance, a chip set including a processor and a memory as shown in FIG. 8. In step 301, the personal health platform 103 calculates a minimum value, a maximum value, or a combination thereof for a physiological condition of a user. By way of example, the minimum and maximum values may correspond to good, average, and bad levels of the one or more physiological conditions associated with a user. By way of further example, the one or more physiological conditions may include any condition associated with a user that has a minimum and a maximum value (e.g., cholesterol, glucose, bodyweight, blood pressure, etc.).

In step 303, the personal health platform 103 senses a measured value for the physiological condition from the user. By way of example, the personal health platform 103 may sense the measured value from one or more biometric devices associated with the user (e.g., a blood pressure cuff, a glucose monitor, a pulse oximeter, a weight scale, etc.). In one embodiment, it is contemplated that the personal health platform 103 can sense the measured value from the one or more biometric devices via one or more short range wireless communications including Bluetooth®, NFC, or a combination thereof.

In step 305, the personal health platform 103 presents a user interface depicting the measured value relative to the minimum value, the maximum value, a historical measured value for the user, or a combination thereof, wherein the user interface depicts the measured value, the minimum value, the maximum value, or a combination thereof on one or more ring-based graphical elements, and wherein the one or more ring-based graphical elements correspond to a measurement range for the physiological condition. By way of example, the user interface may simultaneously depict the measured value as a numeric value surrounded by a ring-based graphical element and a portion of the ring may be rendered as a color corresponding to the respective measurement range of the measured value (e.g., green for a minimum measurement range and red for a maximum measurement range). In addition, the user interface may depict one or more qualitative descriptions of the measured value relative to the minimum value, the maximum value, the historical measured value, or a combination thereof. For example, the user interface may depict the measured value as "good," "average," or "bad" and/or trending up (e.g., with an up arrow) or trending down (e.g., with a down arrow). As previously discussed, the various depictions of the measured value relative to the minimum value, the maximum value, the historical measured value, or a combination thereof may also be rendered based on color (e.g., a good measured value as green, an average measured value as yellow, a bad measured value as red, and so forth).

FIG. 4 depicts a process 400 of calculating a minimum value, a maximum value, or a combination thereof for a physiological condition of a user. In one embodiment, the personal health platform 103 performs the process 400 and is implemented in, for instance, a chip set including a processor and a memory as shown in FIG. 8. In step 401, the personal health platform 103 generates the minimum value, the maximum value, or a combination thereof based on manual input, wherein the manual input is provided by the user, a medical professional, an authorized third-party, or a combination thereof. By way of example, a medical professional (e.g. a clinician) may use a keypad or one or more voice recognition capabilities of a user device to input the minimum and maximum values for the physiological condition of the user (e.g., systolic and diastolic pressures). In addition, a user may input customized minimum and maximum values to set one or more goals (e.g., a desired amount of weight loss during a given period). Further, an authorized third-party (e.g., a user's insurance company) may also input a minimum and a maximum value corresponding to terms of an insurance policy. For example, if the user maintains a certain minimum value over a period of time, the insurance company may offer to reduce the user's overall cost of coverage.

In step 403, the personal health monitor 103 monitors the physiological condition of the user over a period of time to generate a plurality of historical measured values for the user. By way of example, the period of time may correspond to the entire period of treatment, a period of time between visits, a period of time for the presence of a particular physiological condition (e.g., high blood pressure), or a combination thereof. In addition, in one embodiment, it is contemplated that the user may define a customized period of time (e.g., a week or a weekend) to set one or more goals (e.g., an amount of weight loss).

In step 405, the personal health platform 103 calculates the minimum value, the maximum value, or a combination thereof based on the plurality of historical measured values. For example, the personal health platform 103 may determine that over a period of time (e.g., a year) that the minimum weight value for a user was 210 pounds (lbs.) and that the maximum weight value for the user was 230 lbs. As a result, the personal health platform 103 can calculate the minimum value as 210 lbs. and the maximum value as 230 lbs. for the physiological condition of bodyweight based on the plurality of historical measured values.

FIG. 5 depicts a process 500 of presenting a user interface depicting the measured value relative to the minimum value, the maximum value, the historical measured value, or a combination thereof. In one embodiment, the personal health platform 103 performs the process 500 and is implemented in, for instance, a chip set including a processor and a memory as shown in FIG. 8. In step 501, the personal health platform 103 renders the one or more ring-based graphical elements in a concentric arrangement. By way of example, the personal health platform 103 can render an inner concentric ring corresponding to a minimum value and a maximum value, for example, for a physiological condition (e.g., bodyweight) and an outer concentric ring corresponding to a measured value for that physiological condition. In addition, the personal health platform 103 can render a portion of the inner concentric ring corresponding to the minimum value green, for example, the portion of the inner concentric ring corresponding to the maximum value red, for example, and the portion of the outer concentric ring corresponding to the measured value the color corresponding to where the measured value falls within the minimum and maximum values.

In step 503, the personal health platform 103 provides a mode of interaction for operating the user interface, wherein the mode of interaction is based on one or more gestures with the one or more ring-based graphical elements to present a relationship between a potential measured value, the minimum value, the maximum values, or a combination thereof. By way of example, a user can use his or her finger or a pointing device, for example, to drag or rotate the leading edge of the measurement range on the outer concentric circle to discover one or more corresponding values within his or her personalized minimum measurement range, maximum measurement range, or a combination thereof. For example, a user can see how much weight he or she must lose to get within the minimum measurement range.

In step 505, the personal health platform 103 optionally presents a user interface simultaneously depicting a plurality of physiological conditions of the user including the respective measured values relative to the respective minimum values, maximum values, historical measured values, or a combination thereof. By way of example, the personal health platform 103 can simultaneously present the one or more measured values corresponding to a user's blood sugar condition (e.g., LDL, HDL, triglycerides). By way of further example, depending on the device capability information, the resource availability information, or a combination thereof, the personal health platform 103 may present the plurality of physiological conditions based on numeric values, trending characterizations, color, one or more concentric arrangements of the one or more ring-based graphical elements, or a combination thereof.

In step 507, the personal health platform 103 optionally presents a user interface depicting one or more of the plurality of historical measured values in relation to one another. For example, the personal health platform 103 can present a chart depicting a user's weight loss or weight gain over a period of time (e.g., a week, a month, etc.) so that the user may learn whether his or her measured value is trending up or down, for example. As previously discussed, the personal health platform 103 may also depict which values fall within a minimum or a maximum measurement range and/or which values are good, average, or bad, all based on color.

FIGS. 6A-6D are diagrams of user interfaces utilized in the processes of FIGS. 3-5, according to various embodiments.

As shown, the example user interfaces of FIGS. 6A-6D include one or more user interface elements and/or functionalities created and/or modified based, at least in part, on information, data, and/or signals resulting from the processes (e.g., 300, 400, and 500) described with respect to FIGS. 3-5. More specifically, FIGS. 6A-6D illustrate a user interface 601 of a mobile device (e.g., a mobile phone) depicting one or more physiological conditions (e.g., blood sugar) of a user relative to a minimum value, a maximum value, a historical measured value, or a combination thereof associated with the user. In one embodiment, it is contemplated that the user interface 601 is connected to a biometric device (e.g., a glucose monitor)(not shown for illustrative convenience) via one or more short range wireless communications including Bluetooth®, NFC, or a combination thereof.

Figure 6A:
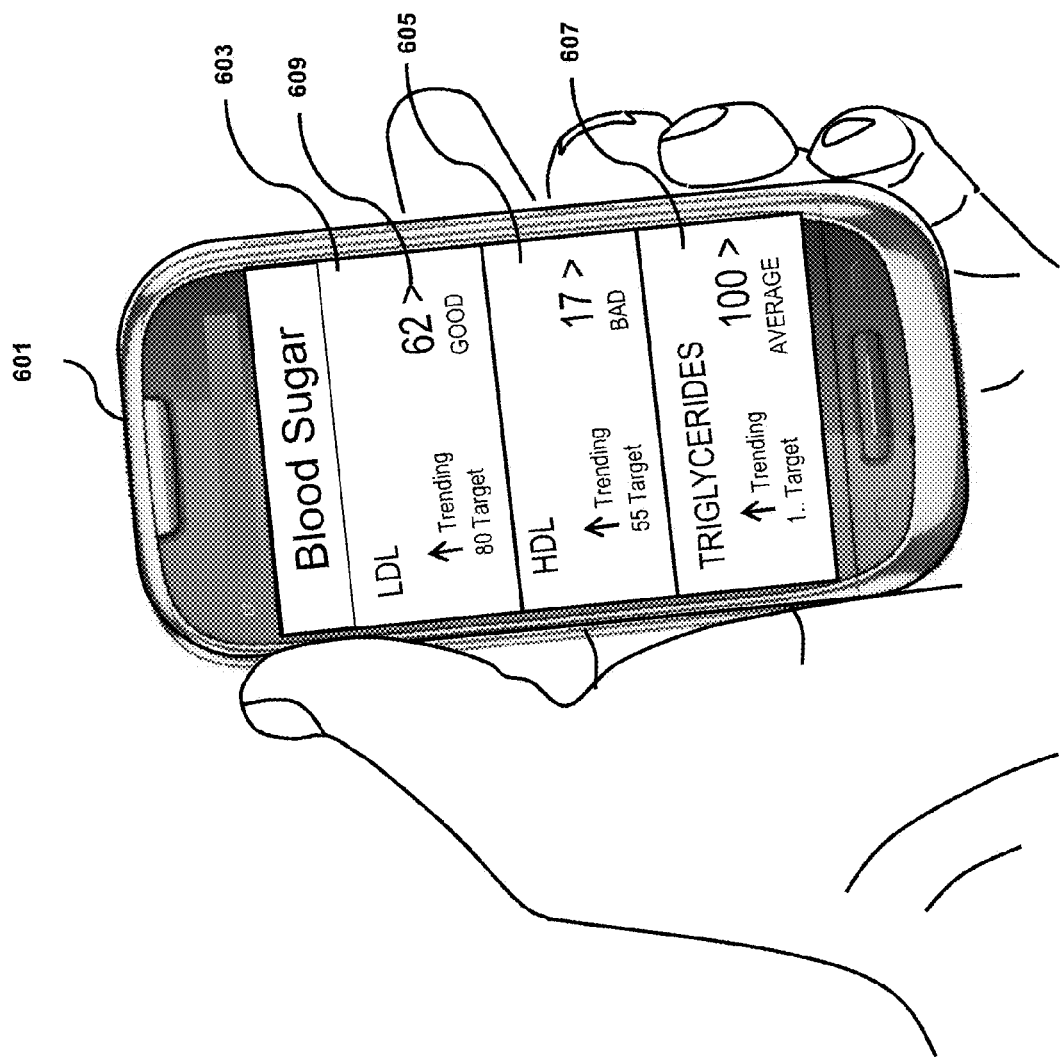
FIGS. 6A-6D are diagrams of user interfaces utilized in the processes of FIGS. 3-5, according to various embodiments.

As previously discussed, in one embodiment, the system 100 can sense one or more measured values (e.g., LDL, HDL, triglycerides) corresponding to a user's blood sugar condition, for example. In one embodiment, the system 100 can present the user interface 601 depicting the one or more measured values and/or a plurality of physiological conditions associated with the user simultaneously, including the respective measured values relative to the respective minimum values, maximum values, historical measured values, or a combination thereof, as depicted in FIG. 6A. For example, element 603 of the user interface 601 indicates that a user's LDL is 62 mg/dl, that the measured value is "good" relative to the user's minimum and maximum values, and that the user's measured value is trending upward relative to one or more historical measured values for the user. Similarly, element 605 of the user interface 601 indicates that the user's HDL is 17 mg/dl, that this measured value is "bad" relative to the user's minimum and maximum values, and that the user's measured value is trending upward relative to one or more historical measures for the user. Further, element 607 of the user interface 601 indicates that the user's triglycerides is 100 mg/dl, that the measured value is "average" relative to the user's minimum and maximum values, and that the user's measured value is trending upward relative to one or more historical measures for the user. In one embodiment, it is contemplated that a user can press the right arrow key 609, double-tap or long-press the element 603, for example, or a combination thereof and the system 100 can present the data associated with a physiological condition (e.g., LDL) in a more graphical manner.

Figure 6B:
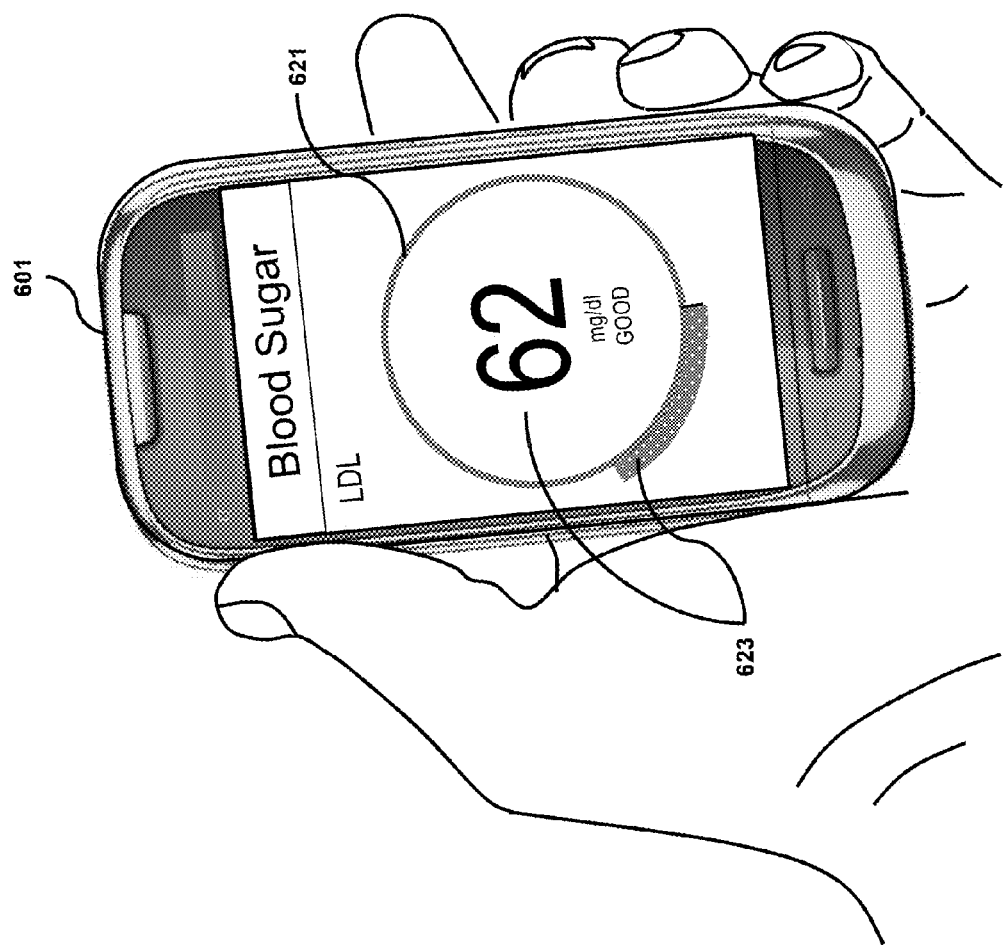

By way of example, FIG. 6B depicts the current LDL condition of a user's blood sugar (e.g., 62 mg/dl) on a ring-based graphical element 621. In one embodiment, the system 100 can present the user interface 601 depicting the measured value 623 relative to the minimum value and maximum values for the user. In particular, the ring-based graphical element 621 and measured value 623 correspond to a measurement range for the physiological condition. For example, the minimum value for a user at a very high risk of heart disease may be below 100 mg/dl. Therefore, in this example use case, the system 100 presents the user's measured value as "good." Further, as previously discussed, the system 100 can present both the quantitative and qualitative aspects of the measured value 623 based on a color (e.g., a green color corresponding to a good value).

Figure 6C:
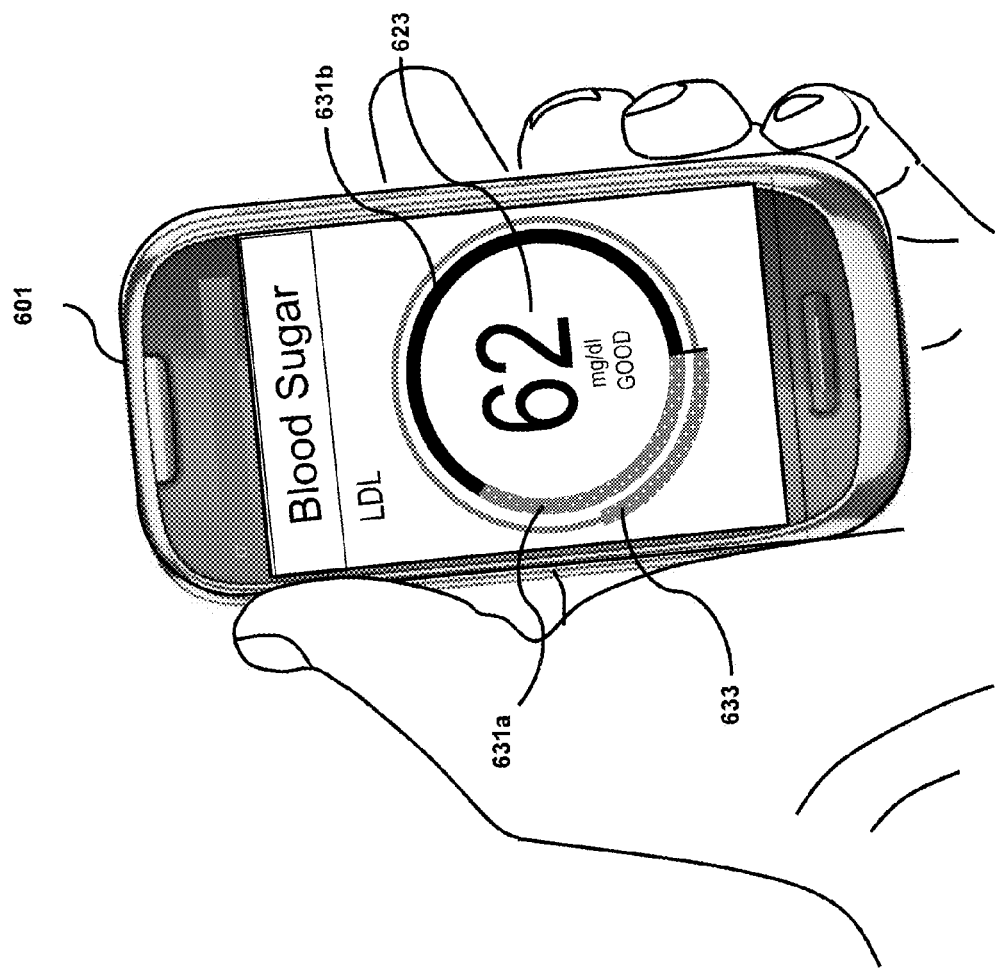

In one embodiment, it is contemplated that the system 100 can present the data associated with a physiological condition (e.g., LDL) in an intuitive and/or interactive manner. For example, in one embodiment, the system 100 can present the user interface 601 depicting a physiological condition (e.g., blood sugar) as one or more ring-based graphical elements in a concentric arrangement (e.g., rings 631 and 633), as depicted in FIG. 6C. By way of example, the system 100 can render the inner concentric ring 631 corresponding to a minimum value (e.g., 0-100 mg/dl)(631a) and a maximum value (e.g., 100-300 mg/dl)(631b) for the blood sugar condition of the user. Moreover, the system 100 can render the portion 631a green, for example, the portion 631b red, for example, and the portion of the outer concentric ring 633 corresponding to the measured value 623, for example, the color corresponding to where the measured value 623 falls within the minimum value 631a and the maximum value 631b. In this example use case, the measured value 623 falls within the portion 631a and therefore the system 100 renders the portion of the concentric ring 633 corresponding to the measured value 623 the same color.

Figure 6D:
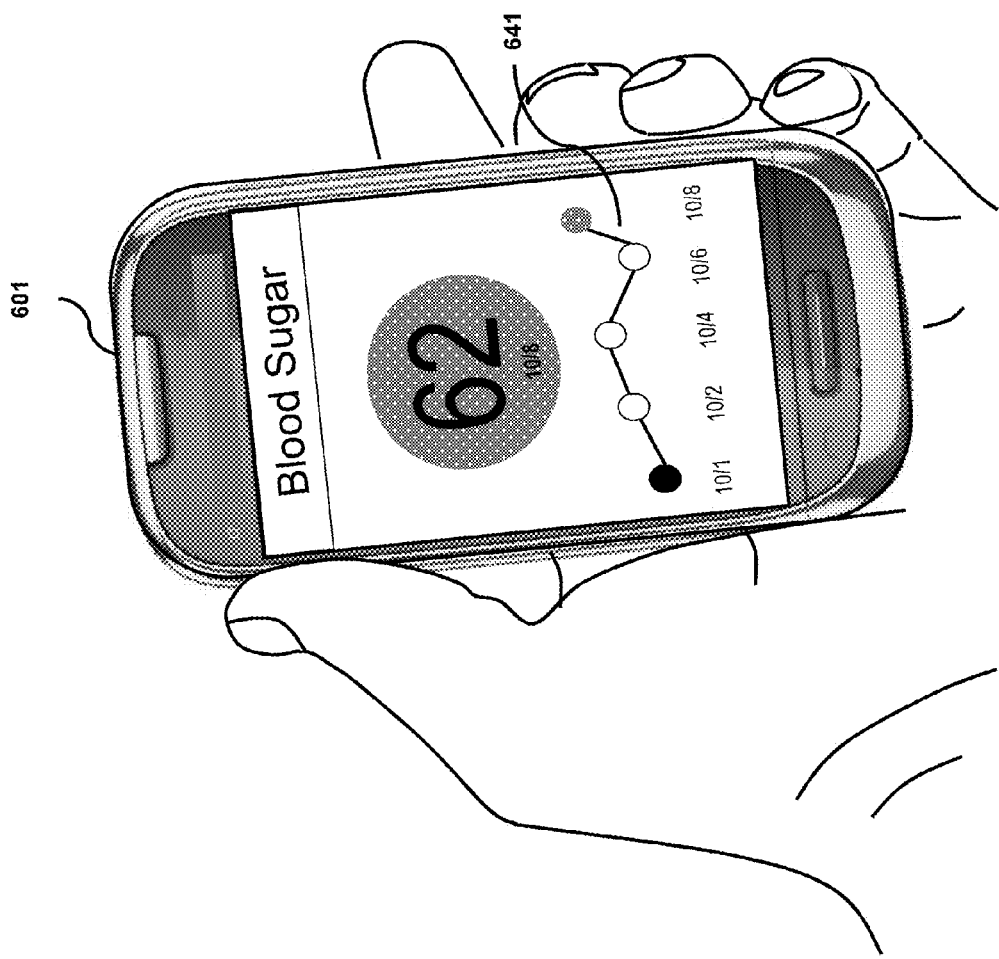

In one embodiment, the system 100 can present the user interface 601 depicting one or more of the plurality of historical measured values in relation to one another, as depicted in FIG. 6D. By way of example, the system 100 can present the historical measured LDL values sensed by the system 100 from the user on 10/1, 10/2, 10/4, 10/6, and 10/10 as a chart 641. As a result, the user, a medical professional (e.g., a clinician), an authorized third-party (e.g., the user's insurance company), or a combination thereof can view and learn whether the user's physiological condition (e.g., blood sugar) is trending up or down, for example. In this example use case, the chart 641 of interface 601 indicates that the LDL levels of the user are trending upwards. In addition, the system 100 can also present a user interface 601 depicting which values fall within the minimum measurement range (e.g., 10/8), the maximum measurement range (e.g., 10/1), or a combination thereof associated with the user and/or which values are good (e.g., 10/8), average (e.g., 10/2-10/6), or bad (e.g., 10/1), all based on color.

Figure 7:
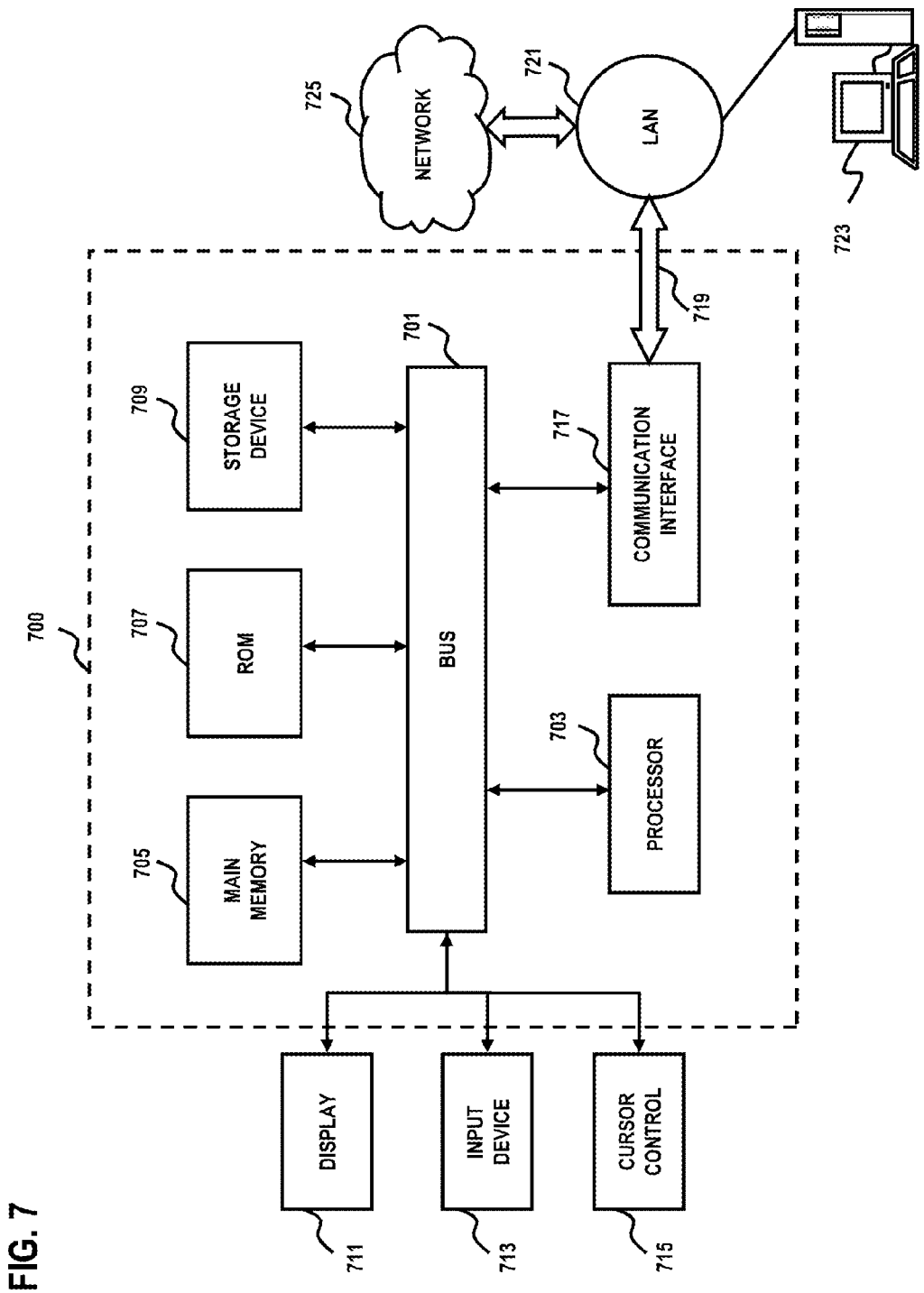
FIG. 7 is a diagram of a computer system that can be used to implement various exemplary embodiments.

FIG. 7 is a diagram of a computer system that can be used to implement various exemplary embodiments. The computer system 700 includes a bus 701 or other communication mechanism for communicating information and one or more processors (of which one is shown) 703 coupled to the bus 701 for processing information. The computer system 700 also includes main memory 705, such as a random access memory (RAM) or other dynamic storage device, coupled to the bus 701 for storing information and instructions to be executed by the processor 703. Main memory 705 can also be used for storing temporary variables or other intermediate information during execution of instructions by the processor 703. The computer system 700 may further include a read only memory (ROM) 707 or other static storage device coupled to the bus 701 for storing static information and instructions for the processor 703. A storage device 709, such as a magnetic disk or optical disk, is coupled to the bus 701 for persistently storing information and instructions.

The computer system 700 may be coupled via the bus 701 to a display 711, such as a cathode ray tube (CRT), liquid crystal display, active matrix display, or plasma display, for displaying information to a computer user. An input device 713, such as a keyboard including alphanumeric and other keys, is coupled to the bus 701 for communicating information and command selections to the processor 703. Another type of user input device is a cursor control 715, such as a mouse, a trackball, or cursor direction keys, for communicating direction information and command selections to the processor 703 and for adjusting cursor movement on the display 711.

According to an embodiment of the invention, the processes described herein are performed by the computer system 700, in response to the processor 703 executing an arrangement of instructions contained in main memory 705. Such instructions can be read into main memory 705 from another computer-readable medium, such as the storage device 709. Execution of the arrangement of instructions contained in main memory 705 causes the processor 703 to perform the process steps described herein. One or more processors in a multi-processing arrangement may also be employed to execute the instructions contained in main memory 705. In alternative embodiments, hard-wired circuitry may be used in place of or in combination with software instructions to implement the embodiment of the invention. Thus, embodiments of the invention are not limited to any specific combination of hardware circuitry and software.

The computer system 700 also includes a communication interface 717 coupled to bus 701. The communication interface 717 provides a two-way data communication coupling to a network link 719 connected to a local network 721. For example, the communication interface 717 may be a digital subscriber line (DSL) card or modem, an integrated services digital network (ISDN) card, a cable modem, a telephone modem, or any other communication interface to provide a data communication connection to a corresponding type of communication line. As another example, communication interface 717 may be a local area network (LAN) card (e.g. for Ethernet™ or an Asynchronous Transfer Model (ATM) network) to provide a data communication connection to a compatible LAN. Wireless links can also be implemented. In any such implementation, communication interface 717 sends and receives electrical, electromagnetic, or optical signals that carry digital data streams representing various types of information. Further, the communication interface 717 can include peripheral interface devices, such as a Universal Serial Bus (USB) interface, a PCMCIA (Personal Computer Memory Card International Association) interface, etc. Although a single communication interface 717 is depicted in FIGS. 6A-6D, multiple communication interfaces can also be employed.

The network link 719 typically provides data communication through one or more networks to other data devices. For example, the network link 719 may provide a connection through local network 721 to a host computer 723, which has connectivity to a network 725 (e.g. a wide area network (WAN) or the global packet data communication network now commonly referred to as the "Internet") or to data equipment operated by a service provider. The local network 721 and the network 725 both use electrical, electromagnetic, or optical signals to convey information and instructions. The signals through the various networks and the signals on the network link 719 and through the communication interface 717, which communicate digital data with the computer system 700, are exemplary forms of carrier waves bearing the information and instructions.

The computer system 700 can send messages and receive data, including program code, through the network(s), the network link 719, and the communication interface 717. In the Internet example, a server (not shown) might transmit requested code belonging to an application program for implementing an embodiment of the invention through the network 725, the local network 721 and the communication interface 717. The processor 703 may execute the transmitted code while being received and/or store the code in the storage device 709, or other non-volatile storage for later execution. In this manner, the computer system 700 may obtain application code in the form of a carrier wave.

The term "computer-readable medium" as used herein refers to any medium that participates in providing instructions to the processor 703 for execution. Such a medium may take many forms, including but not limited to computer-readable storage medium ((or non-transitory)—i.e., non-volatile media and volatile media), and transmission media. Non-volatile media include, for example, optical or magnetic disks, such as the storage device 709. Volatile media include dynamic memory, such as main memory 705. Transmission media include coaxial cables, copper wire and fiber optics, including the wires that comprise the bus 701. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

FIG. 8 illustrates a chip set or chip 800 upon which an embodiment of the invention may be implemented. Chip set 800 is programmed to provide personalized information regarding one or more physiological conditions associated with a user as described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 800 can be implemented in a single chip. It is further contemplated that in certain embodiments the chip set or chip 800 can be implemented as a single "system on a chip." It is further contemplated that in certain embodiments a separate ASIC would not be used, for example, and that all relevant functions as disclosed herein would be performed by a processor or processors. Chip set or chip 800, or a portion thereof, constitutes a means for performing one or more steps of providing personalized information regarding one or more physiological conditions associated with a user.

In one embodiment, the chip set or chip 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a more general purpose processor. Other specialized components to aid in performing the inventive functions described herein may include one or more field programmable gate arrays (FPGA) (not shown), one or more controllers (not shown), or one or more other special-purpose computer chips.

In one embodiment, the chip set or chip 800 includes merely one or more processors and some software and/or firmware supporting and/or relating to and/or for the one or more processors.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform the inventive steps described herein to provide personalized information regarding one or more physiological conditions associated with a user. The memory 805 also stores the data associated with or generated by the execution of the inventive steps.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

Further, to the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well known "opt-in" or "opt-out" processes as may be appropriate for the situation and type of information. Storage and use of personal information may be in an appropriately secure manner reflective of the type of information, for example, through various encryption and anonymization techniques for particularly sensitive information.

What is claimed is:

1. A method comprising:
    calculating, via a processor, a minimum value and a maximum value for a physiological condition of a user;
    sensing a measured value for the physiological condition from the user,
    wherein the sensing includes providing the measured value to the processor using a short range wireless communication;
    presenting a user interface depicting the measured value relative to the minimum value and the maximum value,
    wherein the user interface depicts the minimum value and the maximum value on an inner of two concentric circle ring graphical elements, and the measured value on an outer of the two concentric circle ring graphical elements, wherein each of the two concentric circle ring graphical elements corresponds to a measurement range for the physiological condition, wherein a first arc on the inner of two concentric circle ring graphical elements represents a good measurement range for the physiological condition and is presented in a first color, wherein a second arc on the inner of two concentric circle ring graphical elements represents a bad measurement range for the physiological condition and is presented in a second color, wherein the measured value on the outer of the two concentric circle ring graphical elements is displayed as an arc on the outer of the two concentric circle ring graphical elements in the first color when the sensed measured value falls in the good measurement range and in the second color when the sensed measured value falls in the bad measurement range, wherein the sensed measured value for the physiological condition is further displayed as a numerical value in a center of the two concentric circle ring graphical elements, is displayed in the first color when the sensed measured value falls in the good measurement range, and is displayed in the second color when the sensed measured value falls in the bad measurement range, and wherein the user interface further presents descriptive terms good, average, and/or bad based on the sensed measured value for the physiological condition and further presents an up arrow or down arrow relative to a historical measured value for the user;

monitoring the physiological condition of the user over a period of time to generate a plurality of historical measured values for the user;

calculating the minimum value and the maximum value based on the plurality of historical measured values; and presenting one or more of the plurality of historical measured values in relation to one another in the user interface.

2. A method of claim 1, further comprising:
generating the minimum value and the maximum value based on manual input,
wherein the manual input is provided by the user, a medical professional, an authorized third-party, or a combination thereof.

3. A method according to claim 1, further comprising:
providing a mode of interaction for operating the user interface,
wherein the mode of interaction is based on one or more gestures with the two concentric circle ring graphical elements to present a relationship between a potential measured value, the minimum value, the maximum values, or a combination thereof.

4. A method of claim 1, wherein the user interface depicts the measured value relative to the minimum value, the maximum value, the historical measured value, or a combination thereof based on color.

5. A method of claim 1, further comprising:
presenting simultaneously in the user interface a plurality of physiological conditions of the user including the respective measured values relative to the respective minimum values, maximum values, plurality of historical measured values, or a combination thereof.

6. An apparatus comprising a processor configured to:
calculate a minimum value and a maximum value for a physiological condition of a user;
sense a measured value for the physiological condition from the user,
wherein sensing the measured value includes providing the measured value to the processor using a short range wireless communication;
present a user interface depicting the measured value relative to the minimum value and the maximum value,
wherein the user interface depicts the minimum value and the maximum value on an inner of two concentric circle ring graphical elements, and the measured value on an outer of the two concentric circle ring graphical elements,
wherein each of the two concentric circle ring graphical elements corresponds to a measurement range for the physiological condition,
wherein a first arc on the inner of two concentric circle ring graphical elements represents a good measurement range for the physiological condition and is presented in a first color,
wherein a second arc on the inner of two concentric circle ring graphical elements represents a bad measurement range for the physiological condition and is presented in a second color,
wherein the measured value on the outer of the two concentric circle ring graphical elements is displayed as an arc on the outer of the two concentric circle ring graphical elements in the first color when the sensed measured value falls in the good measurement range and in the second color when the sensed measured value falls in the bad measurement range,
wherein the sensed measured value for the physiological condition is further displayed as a numerical value in a center of the two concentric circle ring graphical elements, is displayed in the first color when the sensed measured value falls in the good measurement range, and is displayed in the second color when the sensed measured value falls in the bad measurement range, and
wherein the user interface further presents descriptive terms good, average, and/or bad based on the sensed measured value for the physiological condition and further presents an up arrow or down arrow relative to a historical measured value for the user;
monitor the physiological condition of the user over a period of time to generate a plurality of historical measured values for the user;
calculate the minimum value and the maximum value based on the plurality of historical measured values; and
present one or more of the plurality of historical measured values in relation to one another in the user interface.

7. An apparatus of claim 6, wherein the processor is further configured to:
generate the minimum value and the maximum value based on manual input,
wherein the manual input is provided by the user, a medical professional, an authorized third-party, or a combination thereof.

8. An apparatus of claim 6, wherein the processor is further configured to:
provide a mode of interaction for operating the user interface,
wherein the mode of interaction is based on one or more gestures with the two concentric circle ring graphical elements to present a relationship between a potential measured value, the minimum value, the maximum values, or a combination thereof.

9. An apparatus of claim 6, wherein the user interface depicts the measured value relative to the minimum value, the maximum value, the historical measured value, or a combination thereof based on color.

10. An apparatus of claim 6, wherein the processor is further configured to:
present simultaneously in the user interface a plurality of physiological conditions of the user including the respective measured values relative to the respective minimum values, maximum values, plurality of historical measured values, or a combination thereof.

11. A system comprising:
a personal health platform configured,
to calculate a minimum value and a maximum value for a physiological condition of a user; to sense a measured value for the physiological condition from the user including providing the measured value to a processor using a short range wireless communication; to present a user interface depicting the measured value relative to the minimum value and the maximum value,
wherein the user interface depicts the minimum value and the maximum value on an inner of two concentric circle ring graphical elements, and the measured value on an outer of the two concentric circle ring graphical elements,
wherein each of the two concentric circle ring graphical elements corresponds to a measurement range for the physiological condition,
wherein a first arc on the inner of two concentric circle ring graphical elements represents a good measurement range for the physiological condition and is presented in a first color,
wherein a second arc on the inner of two concentric circle ring graphical elements represents a bad measurement range for the physiological condition and is presented in a second color,
wherein the measured value on the outer of the two concentric circle ring graphical elements is displayed as an arc on the outer of the two concentric circle ring graphical elements in the first color when the sensed measured value falls in the good measurement range and in the second color when the sensed measured value falls in the bad measurement range,
wherein the sensed measured value for the physiological condition is further displayed as a numerical value in a center of the two concentric circle ring graphical elements, is displayed in the first color when the sensed measured value falls in the good measurement range, and is displayed in the second color when the sensed measured value falls in the bad measurement range, and
wherein the user interface further presents descriptive terms good, average, and/or bad based on the sensed measured value for the physiological condition and further presents an up arrow or down arrow relative to a historical measured value for the user;
to monitor the physiological condition of the user over a period of time to generate a plurality of historical measured values for the user; and to calculate the minimum value and the maximum value based on the plurality of historical measured values; and
present one or more of the plurality of historical measured values in relation to one another in the user interface.

12. A system of claim 11, further comprising:
the personal health platform further configured to generate the minimum value and the maximum value based on manual input,
wherein the manual input is provided by the user, a medical professional, an authorized third-party, or a combination thereof.

13. A system of claim 11, further comprising:
the personal health platform further configured to provide a mode of interaction for operating the user interface,
wherein the mode of interaction is based on one or more gestures with the two concentric circle ring graphical elements to present a relationship between a potential measured value, the minimum value, the maximum values, or a combination thereof.

* * * * *